United States Patent [19]
Lorincz

[11] Patent Number: 5,812,312
[45] Date of Patent: Sep. 22, 1998

[54] MICROSCOPE SLIDE

[76] Inventor: Andrew Endre Lorincz, 3628 Belle Meade Way, Mountain Brook, Ala. 35223-1508

[21] Appl. No.: 929,234

[22] Filed: Sep. 4, 1997

[51] Int. Cl.[6] .............................. G02B 21/34; G01N 21/00
[52] U.S. Cl. ......................... 359/397; 359/396; 359/398; 422/58; 427/2.11
[58] Field of Search ................................... 359/396, 397, 359/398; 422/58; 427/2.11

[56] References Cited

U.S. PATENT DOCUMENTS

| | | |
|---|---|---|
| 3,532,412 | 10/1970 | Miller . |
| 3,551,023 | 12/1970 | Tolles ....................................... 359/398 |
| 3,556,633 | 1/1971 | Mutschmann et al. . |
| 3,930,928 | 1/1976 | Tapert . |
| 4,171,866 | 10/1979 | Tolles ....................................... 359/398 |
| 4,188,246 | 2/1980 | Lipshaw . |
| 4,302,180 | 11/1981 | Fischer et al. . |
| 4,545,831 | 10/1985 | Ornstein ................................... 156/57 |
| 4,635,790 | 1/1987 | Jackson et al. . |
| 4,935,374 | 6/1990 | Jacobs et al. . |
| 5,364,790 | 11/1994 | Atwood et al. . |

OTHER PUBLICATIONS

Lorincz et al., Supravital Microscope Fluorescence Technique Used to Identify Spirochetes, Annals of Clinical and Laboratory Science, 19:313–314 (1989).
Lorincz, Andrew E., One Step On–Site Epi–Fluorescence Detection of Fungi: A Possible Alternative to KOH Screening. Annals of Clinical and Laboratory Science, 23:307 (1993).
Lorincz, Andrew E., Direct Visualization of Mycoplasma via Supravital Staining and Fluorescence Microscopy, Israel J of Med, 5:543 (1987).
Lorincz, Andrew E., Rapid Method of the Identification of Mycoplasma Organisms. Manual of Procedures for the Application on Nucleic Acid Probes & Monoclonal Antibodies and Human Disease, pp. 163–165 (1987).
Hiraoka et al., Diagnosis of urinary tract infection by urine microscopy using a disposable counting chamber. Scand J Clin Lab Invest, 53:705–709, (1993).
Petcharuttana et al, Fluorescence microscopy of DES–induced morphologic transformation in unfixed, cultured cells. J Oral Pathol Med, 18:451–456 (1989).

Primary Examiner—Jon W. Henry

[57] ABSTRACT

A self-staining microscopic slide designed for immediate staining and viewing of cells in biological fluid and tissue samples, preferably with an epi-fluorescence microscope. The pre-prepared microscope slide preferably has a supravital fluorescent stain applied thereon, which is overlaid with a transparent tape or film. During use, the film is peeled back to expose the stain so that a sample can be applied thereon for intermixture therewith. The film is then replaced over the stained sample to act as a cover slip for immediate viewing. Living cells and microorganisms are rendered dramatically visible and cellular dysmorphology can be readily ascertained. The time and cost associated with preparing a fixed and sectioned sample is completely avoided as well as the problem of artifacts and sample fragmentation found in fixed preparations. The slide can include reference standards to facilitate microscope focusing, and to allow measurements of cells and microorganisms. An alternate embodiment provides a flexible microscope slide which can be folded over such that a viewing portion of the slide can be placed against a specimen to obtain a sample directly therefrom without the need of transferring devices, thereby reducing biological hazards. This novel slide permits on-site, point-of-care screening in a matter of minutes of any biological fluid or tissue sample for presence of infectious agents.

19 Claims, 2 Drawing Sheets

MICROSCOPE SLIDE

FIELD OF THE INVENTION

The present invention relates to microscope slides. More particularly, the present invention relates to an improved microscope slide designed for supravital staining of biological fluids and tissues.

BACKGROUND OF THE INVENTION

Presently used methods for analyzing biological specimens for cellular dysmorphology and microbial infection are both time consuming and costly. For example, tissue samples taken from patients, such as needle biopsies and aspirates, typically must be chemically fixed and stained, and oftentimes sectioned, and then prepared on microscope slides before they can be examined. Additionally, in many circumstances, biological samples must first be cultured before the processing steps mentioned above. Another problem concerns the resulting specimen itself which is usually substantially altered by fixation and fragmentation during the preparation process.

Another problem concerns unnecessary procedures, which again waste time and resources. In a typical urinalysis, for example, a sample is obtained from a patient and subjected to a "dipstick" screening procedure. Light microscopic examination of the sediment following centrifugation of the urine specimen is then performed. If there are any abnormal results from these examinations, the sample is transferred to a laboratory for microbiological culture and antibiotic sensitivity studies, which typically take from 24 to 48 hours, or longer, to obtain the results. However, in many instances as much as 80% of the urine samples submitted for culture and sensitivity studies do not result in the detection of clinically significant bacterial presence, thus wasting valuable technician time and laboratory material resources. Furthermore, in rural areas or third world countries, samples must typically be transported to remote locations for evaluation, which can magnify the problem due to additional time delays, plus additional transportation and handling costs. At present, there are no rapid (e.g. less than 5 minutes) on-site screening methods to ascertain whether further testing of a biological sample (e.g. urine) is necessary.

The present invention represents a departure from standard microbial and morphologic studies in the practice of clinical medicine by modifying microscope slides to be used as screening tools for on-site determination of possible infection or presence of cellular dysmorphology. The slides of the present invention avoid the time associated with preparing traditional slide preparations and they further provide a simpler and less expensive alternative to the currently utilized microscopy screening procedures, such as the Gram histochemical stain used to detect bacteria and other microorganisms; the potassium hydroxide (KOH) preparation used to screen for fungi and yeast; and the darkfield examination used to detect spirochetes and other microorganisms less than 1 micrometer (uM) in diameter or size, such as mycoplasma, other mollicutes, legionella, etc.

SUMMARY OF THE PRESENT INVENTION

It is an object of the present invention to provide a self-staining microscope slide adapted for supravital staining of cells in a biological fluid or tissue sample.

It is another object of the present invention to provide a self-staining microscope slide which allows for immediate on-site screening of a biological fluid or tissue sample.

It is another object of the present invention to provide a self-staining microscope slide which permits greatly enhanced visualization of the stained sample when viewed with an epi-fluorescent microscope.

It is another object of the present invention to provide a self-staining microscope slide which overcomes the problem of artifacts due to fixation and sample fragmentation.

It is another object of the present invention to provide a self-staining microscope slide which includes references to facilitate microscope focusing.

It is yet another object of the present invention to provide a microscope slide which is flexible to allow the slide to be folded over such that a viewing portion of the slide can be placed against a specimen to obtain a sample directly therefrom without the need of transferring devices or breakable glass components.

These and other objects of the present invention are accomplished through the use of a self-staining microscopic slide designed for immediate staining and viewing of cells in biological fluid and tissue samples, preferably with an epi-fluorescence microscope. The pre-prepared microscope slide preferably has a supravital fluorescent stain applied thereon, which is overlaid with a transparent tape or film. During use, the film is peeled back to expose the stain so that a sample can be applied thereon for intermixture therewith. The film is then replaced over the stained sample to act as a cover slip for immediate viewing. Living cells and microorganisms are rendered dramatically visible and cellular dysmorphology can be readily ascertained. The time and cost associated with preparing a fixed and sectioned sample is completely avoided as well as the problem of artifacts and sample fragmentation found in fixed preparations. The slide can include reference standards to facilitate microscope focusing, and to allow measurements of cells and microorganisms. An alternate embodiment provides a flexible microscope slide which can be folded over such that a viewing portion of the slide can be placed against a specimen to obtain a sample directly therefrom without the need of transferring devices, thereby reducing biological hazards. This novel slide permits on-site, point-of-care screening in a matter of minutes of any biological fluid or tissue sample (e.g. urine, blood, sputum, spinal fluid, amniotic fluid, tears, needle aspirates, semen, tissue touch preparations, plant sap, etc.) for presence of infectious agents (e.g. bacteria, including mycoplasma-sized mollicutes, spirochetes, fungi, parasites, etc.).

These and other objects and advantages of the invention mill become apparent from the following detailed description of the preferred embodiment of the invention.

BRIEF DESCRIPTION OF THE DRAWINGS

A microscope slide embodying features of the invention is described in the accompanying drawings which form a portion of this disclosure and wherein.

DETAILED DESCRIPTION OF THE PREFERRED EMBODIMENT

A more complete understanding of the present invention may be obtained by reference to the accompanying drawings. The present invention is a self-staining microscope slide designed for supravital staining of cells and microorganisms in a biological fluid or tissue sample, and adapted for immediate visual or instrumental examination of the stained cells. The American Heritage Dictionary of the English Language (3rd ed., 1992) defines "supravital" as relating to or capable of staining living cells after their removal from a living or recently dead organism. Thus, the present invention allows immediate, on-site staining of unfixed cells from a biological sample which can be immediately viewed for preliminary diagnosis of a plurality of conditions. Since supravital staining is incorporated in the prepared slides, the time and cost of drying, chemical fixation, and/or sectioning of specimens may be completely avoided.

Figure 1:
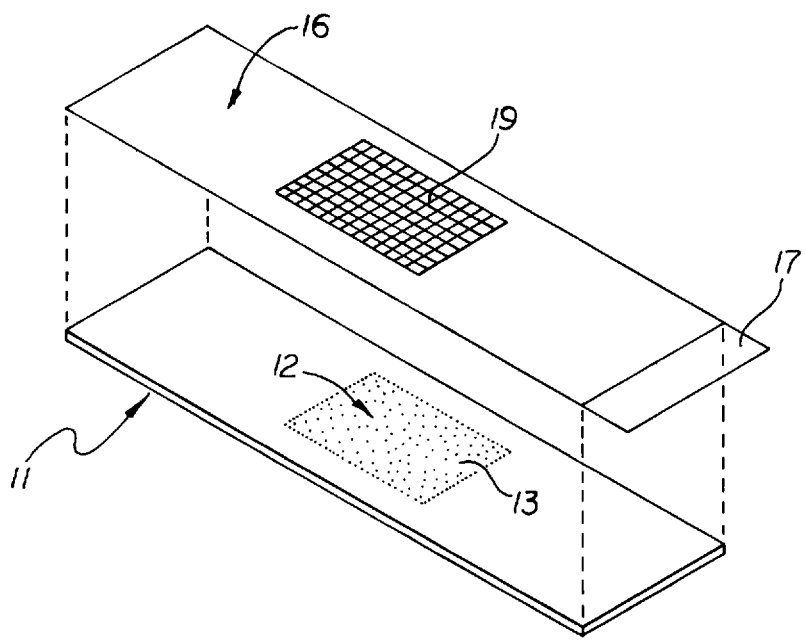
FIG. 1 is an exploded perspective view of the present invention.
Figure 2:
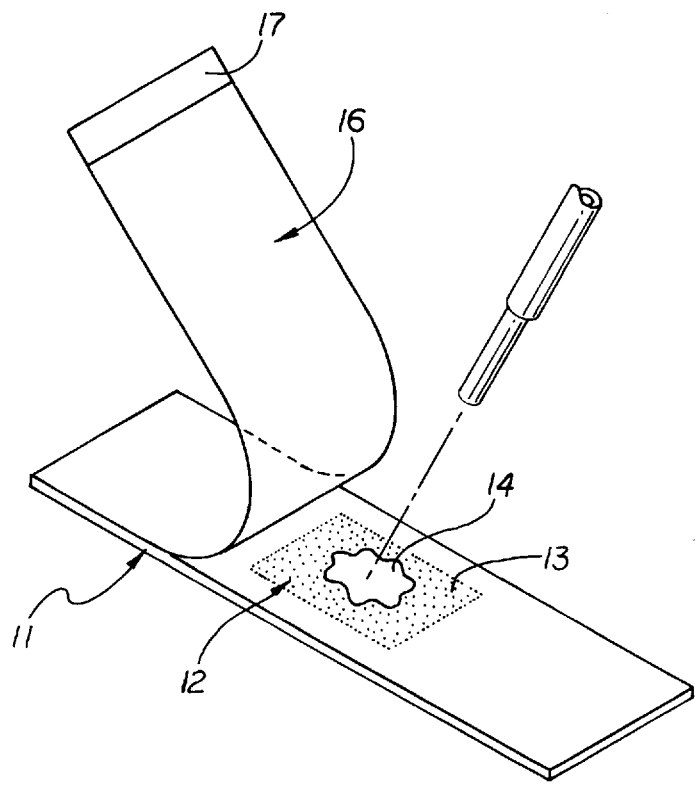
FIG. 2 is a perspective view of the present invention illustrating, the cover film peeled back so that a sample can be added to the slide.

The preferred embodiment of the present invention, shown in FIGS. 1 and 2, comprises a microscope slide 11 having a viewing area 12, a dye 13 applied to the viewing area 12 for staining a biological sample 14, and a flexible transparent tape or film 16 attached to the slide 11 by means of a weak adhesive (not shown) such that the film 16 can be peeled back to expose the viewing area 12 for placement of the biological sample 14 thereon for intermixture with the dye 13, and replaced such that the stained sample can be viewed under a microscope. Alternatively, the dye 13 can be applied to the film 16 at a location opposite the viewing area 12 of the slide 11. For example, the dye may be admixed with the adhesive on the film.

Figure 5:
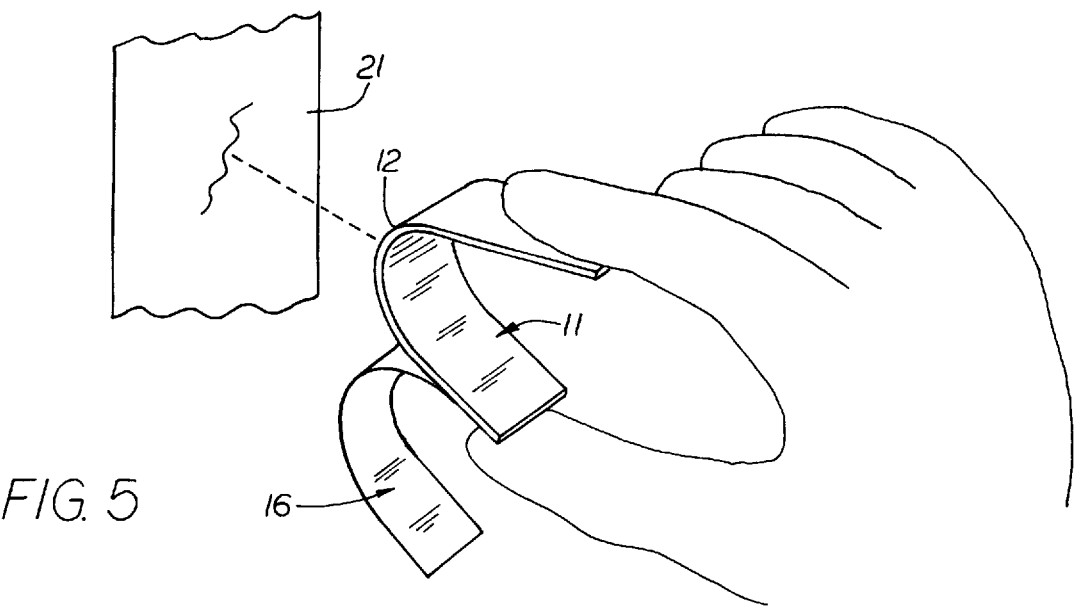
FIG. 5 is a perspective view of another alternate embodiment of the present invention.

The microscope slide can be either rigid or flexible. Rigid slides are well known in the art and typically comprise glass or hardened plastic; however, flexible slides are not previously known in the art. A flexible slide allows the slide 11 to be folded over or bent such that the viewing area 12 is presented to be touched directly to the specimen or suspected tissue lesion 21 (e.g. syphilitic chancre) in order to obtain a sample therefrom, as illustrated in FIG. 5. This removes the need for transferring means, such as a swab, and reduces the hazards and requirements for increased waste disposal of transfer equipment. The flexible slide is most appropriate for collecting specimens now examined by darkfield microscopy, e.g. in sexually transmitted disease clinic settings where glass slides and cover slips pose an added risk to the person collecting the specimen. The flexible slide also has the advantage of accessing difficult anatomical sites not readily reachable by a rigid slide or cover slip. Flexible slides preferably comprise a transparent plastic material, such as polycarbonates, cellular acetate, polyvinyl chlorides, or other polymers and polymer condensation products.

The preferred embodiment utilizes a plastic slide because it is lightweight and not as prone to breakage as glass slides. The plastic slides can be easily sterilized (e.g. via autoclave or microwave oven) for disposal. Additionally, these slides can be recycled to reduce biological wastes. The light weight feature of the plastic slides facilitates transport and storage. One surface side is preferably pitted, or roughened, to achieve a "frosted" appearance (not shown), a feature well known in the art. This has several benefits, including assisting in the application of the supravital stain by promoting its dispersion on and adherence to the slide surface, and allowing the slide to be easily marked for archival purposes.

The supravital dyes are preferably water soluble fluorochromes, such as acridine orange, acridine yellow, etc., in appropriately buffered concentrations. A fluorescence or epi-fluorescence microscope is required to view the fluorescent stained samples, and the latter if frosted slides are used because the frosted slide effects fluorescent light dispersion therethrough. By staining the sample with a fluorochrome and utilizing an epi-fluorescent microscope for viewing, the visualization of the structures in the sample is greatly enhanced compared to visualization with phase contrast or similar light microscopy. This is analogous to viewing the moon at night compared to viewing the moon during the day. The vital dye will diffuse into a living cell or microorganism, without killing the cell, and complex with macromolecules such as DNA, glycosaminoglycans, lipopolysaccharides, etc., which are present in the cell. The dye-macromolecule complexes are rendered fluorescent and can be visualized after excitation with appropriate light frequencies from mercury lamps, halogen lamps, tungsten lamps, etc.

The film 16 comprises a flexible transparent material having an adhesive on one side, such as Scotch™ brand tapes (3 M Company), for placement over the frosted surface of the slide 11 such that the adhesive surface is in contact with the frosted surface of the slide. In an alternate embodiment, the adhesive can be placed only along the margins of the film so that no adhesive overlaps the dye. The film 16 preferably has a portion 17 on at least one end having no adhesive thereon such that the portion 17 acts as a grip for handling the film 16. Film 16 can be applied only to the frosted surface of the slide 11, or it can be applied so that at least one end of film 16 overlaps the side or under surface of the slide 11 (not shown).

Figure 4:
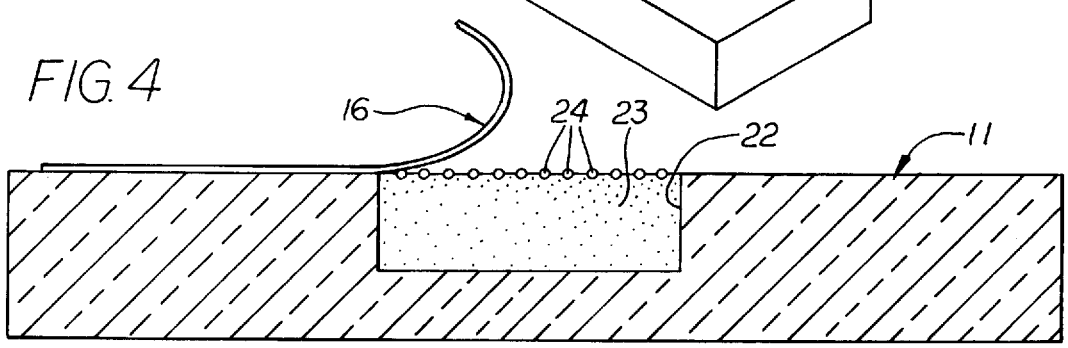
FIG. 4 is a cross-sectional view of the embodiment of FIG. 3.

Other features which are beneficial include the addition of size references, such as fluorescent microspheres of known dimension (e.g. 1 uM), to the surface of the slide or the film such that they coincide with the field of focus of the specimen. For example, the microspheres can be attached to the adhesive on the film or the microspheres may be placed in the dye before application of the dye to the slide such that they are held to the slide with the subsequently dried dye. Microspheres 24 applied to the surface of culture media 23 are illustrated in FIG. 4. This facilitates focusing the microscope and provides an internal reference standard for size, which is preserved for photomicrography or video image capture. Other reference standards, such as a sizing grid 19 or the like, can also be incorporated as by etching or photographic reproduction onto the surface of the slide or film to allow sizing and quantitation of cells, microorganisms or the like.

To prepare the self-staining slide of the preferred embodiment, a plastic microscope slide 11 having a predetermined size is selected. A dye 13, preferably a buffered fluorochrome such as acridine orange, is applied over a designated viewing area 12 of the "frosted" surface of the slide 11 and dried. The frosted surface has a greater surface area than a smooth surface, therefore providing a greater area for the dye to dry upon. Accordingly, a larger quantity of dye can be available for rehydration. As noted above, the dye may alternatively be incorporated into the adhesive on the film. The transparent film 16 is placed over the frosted surface of the slide 11. When the slide is ready to be used, the transparent film 16 is peeled back to expose the viewing area 12 having the dye 13 thereon, a sample 14 of biological fluid (typically 25–50 microliters) or a tissue touch preparation is applied to the slide in the area containing the dye 13, and the adhesive film 16 is returned to its sealed state to act as a cover slip. In the case of a tissue touch preparation, the tissue sample, such as a sliver from a needle biopsy, is typically placed onto the slide and lightly compressed to expel tissue fluids containing cells and possible microorganisms onto the slide surface. Buffered solutions to promote rehydration of the vital dye can also be used. Microscope immersion oil is placed on the film 16 over the viewing area 12, and an epi-fluorescence microscope using typically a 40× or 100× oil immersion objective is used to view the sample.

Since the collected biological fluid sample (e.g. blood, urine, sputum, bronchial or gastric washings, spinal fluid, synovial fluid, cervical smear, semen, prostate secretion, tears, needle biopsy specimens, amniotic fluid, plant sap, etc.) is not dried or chemically fixed, the morphology and mobility of the intact cells and/or microorganisms is maintained. Nuclear morphology of the living cells is preserved for immediate visual (or image) analysis facilitating determination of the presence or absence of malignant dysmorphology. Similarly, the presence of abnormal macromolecular "storage" in cell (e.g. in amniotic fluid, white blood cells, cultured fibroblasts) can be readily observed. Although all DNA containing cells are non-specifically stained by the fluorochrome, the size, shape and movement patterns of any microorganisms present may be helpful in serving for preliminary identification of the microorganisms. Additionally, the presence or absence of viral inclusion bodies can also be observed, which is of some consequence in examining oral and nasal smears.

Figure 3:
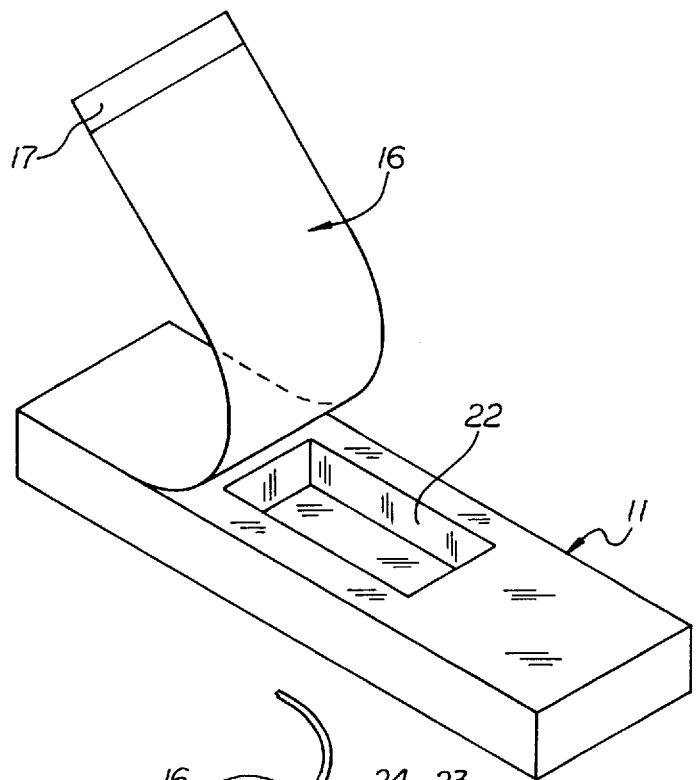
FIG. 3 is a perspective view of an alternate embodiment of the present invention.

Another beneficial feature is to modify the slides for culture and/or transport by incorporating a well 22 having culture media 23 (e.g. Sabouraud's agar for fungi) therein, illustrated in FIGS. 3 and 4. Any sized or shaped well can be created.. Furthermore, the dye can be incorporated into the culture medium. The slide can be used for screening and then be transported to a central lab for culture and/or definitive identification.

Nowadays, with the availability of portable fluorescence microscopes that can even be powered by an automobile battery, the ability to use the slides can be readily adapted for field use in developing countries, rural clinics, mobile vans, etc. If visual screening confirms the presence of bacterial or fungal infection, or protozoan infestation, the same specially prepared slides that are used for on-site screening, can be used for specimen transfer. Such transfer to a peripheral or reference laboratory permits further culture as well as definitive identification via histochemical study or DNA analysis (e.g. PCR, ELISA, monoclonal antibody studies). The slides preserve the microorganism intact and if the appropriate culture medium suited for optimal growth is incorporated into the slide, the need to take a second sample for culture is precluded and the need for subculturing by the reference lab may also be avoided. Furthermore, photomicrographs or digital imaging techniques can permanently capture what can be visualized in the epi-fluorescence microscope. Transmission of these digital images to remote central laboratories for evaluation is also a possibility.

By utilizing the slides in the operating room, examination of biopsy tissue touch preparations or needle biopsies might obviate the need for the expensive microtomes and cytotechnicians now required for present quick-frozen tissue section studies. Turnaround times for results would also be considerably faster. The delays between specimen collection and reporting of laboratory results do not exist when testing is conducted on-site, which permits immediate action by the physician once testing is completed. Thus, this methodology should significantly improve clinical practice guidelines for physicians ordering laboratory tests. For example, an uncentrifuged, supravitally stained urine sample on the present slide can be immediately visualized with an epi-fluorescent microscope, allowing superior visualization of the structures in the sample to substantially increase the accuracy of diagnosing urinary tract infections. The principle and methodology are scientifically accurate, reproducible, easily taught and easily learned; even by nonprofessional laboratorians. The slides can also be used to examine plant specimens, such as plant sap, for microbial infections and the like.

The slides of the present invention provide a simpler and less expensive alternative to the currently utilized microscopy screening procedures, such as the Gram histochemical stain used to detect bacteria and other microorganisms; the potassium hydroxide (KOH) preparation used to screen for fungi and yeast; and the darkfield examination used to detect spirochetes. Additionally, the slides permit detection of mycoplasma species and other mollicutes (smallest known bacteria that do not have cell walls), which cannot be visualized by standard light transmission microscopes.

Production cost of plastic and/or film vita-cult screening slides should be less expensive than the cost of producing glass microscope slides and glass cover slips. Chances for breakage and infecting clinical personnel should be diminished. The quantity of cultural media required is considerably less than now used in traditional petri dish culture plates or slant tube culture equipment. The weight of the slides is far less than that of glass slides or culture plates, thus facilitating transport and storage. Importantly, laboratory wastes is concomitantly reduced.

It is to be understood that the form of the invention shown is a preferred embodiment thereof and that various changes and modifications may be made therein without departing from the spirit of the invention or scope as defined in the following claims.

Having set forth the nature of the invention, what is claimed is:

1. An apparatus for staining cells and microorganisms in a biological sample for viewing with an epi-fluorescence microscope, comprising:
   a) a microscope slide having a viewing area;
   b) a fluorochrome for staining the biological sample; and
   c) a flexible transparent film attached to said slide with an adhesive such that said fluorochrome is in contact with said viewing area between said slide and said film, wherein said film can be removed to expose said viewing area for placement of the biological sample thereon and replaced such that the sample can be viewed under the microscope.

2. An apparatus according to claim 1 wherein said slide comprises a plastic material having a roughened surface.

3. An apparatus according to claim 1 wherein said fluorochrome comprises acridine orange.

4. An apparatus according to claim 1 wherein said fluorochrome comprises reference markers to assist in focusing the microscope.

5. An apparatus according to claim 1 wherein said apparatus further comprises a reference standard for measuring the size and quantity of cells or microorganisms in the sample.

6. An apparatus according to claim 5 wherein said reference standard comprises a grid printed on said film.

7. An apparatus according to claim 5 wherein said reference standard comprises a grid printed on said slide.

8. An apparatus according to claim 1 wherein said viewing area comprises a well formed in said slide.

9. An apparatus according to claim 8 wherein said fluorochrome is within said well.

10. An apparatus according to claim 8 wherein said well has culture medium therein.

11. An apparatus according to claim 10 wherein said culture medium has said fluorochrome mixed therewith.

12. An apparatus according to claim 1 wherein said slide is flexible such that said slide can be folded over such that said viewing area can be placed against a specimen to obtain a sample directly therefrom.

13. An apparatus for staining a biological sample for viewing with a microscope, comprising:

a) a microscope slide having a viewing area;
   b) a dye for staining the biological sample; and
   c) a flexible transparent film attached to said slide with an adhesive such that said dye is in contact with said viewing area between said slide and said film, wherein said film can be removed to expose said viewing area for placement of the biological sample thereon and replaced such that the sample can be viewed under the microscope.

14. An apparatus according to claim 13 wherein said dye comprises reference markers to assist in focusing the microscope.

15. An apparatus according to claim 13 wherein said viewing area comprises a well formed in said slide.

16. An apparatus according to claim 15 wherein said well has culture medium therein.

17. An apparatus according to claim 16 wherein said culture medium has said dye mixed therewith.

18. An apparatus according to claim 13 wherein said slide is flexible such that said slide can be folded over such that said viewing area can be placed against a specimen to obtain a sample directly therefrom.

19. A microscope slide for immediate presentation of supravital specimens for viewing, comprising in combination:

a) means for supporting a specimen for positioning within the viewing area of a microscope;
   b) flexible transparent means for resealably covering a first surface of said supporting means and said specimen supported thereon; and
   c) means for fluorochrome staining said specimen, said staining means interspersed between said supporting means an said flexible transparent means such that placement of said specimen on said supporting means induces such staining.

* * * * *